(12) United States Patent
Cohen

(10) Patent No.: US 6,423,352 B2
(45) Date of Patent: Jul. 23, 2002

(54) ALKALINE PREPARATIONS OF INULA FOR THE CONTROL OF FUNGAL DISEASES IN PLANTS

(75) Inventor: Yigal Cohen, Kiryat Ono (IL)

(73) Assignee: Inulex Ltd., Ofakim (IL)

( * ) Notice: Subject to any disclaimer, the term of this patent is extended or adjusted under 35 U.S.C. 154(b) by 0 days.

(21) Appl. No.: 09/781,164

(22) Filed: Feb. 13, 2001

Related U.S. Application Data

(62) Division of application No. 09/233,971, filed on Jan. 20, 1999, now abandoned.
(60) Provisional application No. 60/072,356, filed on Jan. 23, 1998.

(51) Int. Cl.[7] ................................................ A61K 35/78
(52) U.S. Cl. ........................ 424/764; 424/725; 424/773; 424/405; 424/774; 424/779
(58) Field of Search ................................ 424/725, 764, 424/774, 779, 195.15, 405

(56) References Cited

U.S. PATENT DOCUMENTS

| 3,920,844 A | * | 11/1975 | Barer et al. |
| 5,212,183 A | * | 5/1993 | Himmele et al. |
| 5,438,066 A | * | 8/1995 | Matthews |
| 6,139,879 A | * | 10/2000 | Taylor |

FOREIGN PATENT DOCUMENTS

| EP | 006 060 A1 | * | 12/1979 |
| EP | 306413 A1 | * | 3/1989 |

OTHER PUBLICATIONS

Yegen et al., Zeitschrift fuer Pflanzenkrankheiten und Pflanzenschutz, 1992, vol. 99, No. 4, pp. 349–359, abstract.*

* cited by examiner

Primary Examiner—Leon B. Lankford, Jr.
Assistant Examiner—Ruth Davis
(74) Attorney, Agent, or Firm—G. E. Ehrlich Ltd.

(57) ABSTRACT

Rapid, convenient and inexpensive methods for preparing fungicidal suspensions from Inula are described. Methods for controlling fungal disease and crops by using alkaline solutions are also disclosed.

11 Claims, No Drawings

ALKALINE PREPARATIONS OF INULA FOR THE CONTROL OF FUNGAL DISEASES IN PLANTS

This application claims priority of U.S. Provisional Application Ser. No. 60/072,356 filed Jan. 23, 1998 and is a Divisional application of Ser. No. 09/233,971 filed Jan. 20, 1999, now abandoned.

FIELD OF THE INVENTION

The subject invention relates an anti-fungal preparation for the control of fungal diseases in plants, more specifically, to alkaline extracts of Inula which are highly active in controlling diseases caused by fungi in crop plants.

BACKGROUND OF THE INVENTION

Extracts of plants which are members of the Inula species are effective against infections of plants caused by a variety of fungi. These extracts are typically prepared by dipping freshly cut Inula shoots in an organic solvent or by agitating freshly cut or dried Inula shoots in an organic solvent, removing the solvent to form a paste, and then dissolving the paste in an organic solvent or in water, possibly with an additive. Alternatively, suspensions of Inula can be prepared by grinding dried Inula shoots into a fine powder, adding an emulsifier, and then suspending the mixture in water. In both cases, the resultant preparation is then applied to plants resulting in the control of a wide variety of fungal diseases. Extracts of suspensions of Inula plants are effective at low concentrations, in the range of fractions of a single percent of extract, such that dilute concentrations have excellent fungal-control properties.

The plants which are the basis of these fungicidal extracts and suspensions are *Inula viscosa* and *Inula graveolens* (Family Compositae), perennial weeds widespread in the Mediterranean Basin.

Methods of preparing aqueous extracts from various parts of the Inula plant are well known in the literature. Additionally, organic extracts of the Inula plant are also well known in the art, e.g., U.S. Pat. No. 5,837,253. However, the prior art indicates that aqueous extracts of Inula shoots are poorly effective against fungal diseases of crop plants whereas extracts made with organic solvents are highly effective anti-fungal agents.

Methods have also been described for using organic solvents to extract Inula plants, but these are clearly distinguished from that disclosed in U.S. Pat. No. 5,837,253. Two of the prior art methods involved contacting the whole Inula plant, or the aerial parts thereof, with an organic solvent either by maceration of the plant in the organic solvent or by percolation of the solvent through the plant. Furthermore, U.S. Pat. No. 4,254,112 to Debat et al., (hereinafter referred to as "Debat") describes the preparation of extracts of *Inula viscosa* and *Inula graveolens* using whole Inula plants which have been dried and ground and organic solvents, by using a Soxhlet apparatus. The yield of the paste obtained by this method was approximately 1.75–4%. U.S. Pat. No. 5,176,193 to Honerlagen et al. (hereinafter referred to as "Honerlagen") describes a process for preparing a partial extract from roots of *Inula helenium* which involves contacting the plant material with an organic solvent, adding a drying agent to the solution to remove the water, removing the drying agent, and then distilling the dried organic phase. By contrast, the method disclosed in U.S. Pat. No. 5,837,753 disclosed either briefly dipping the leaves and stems of the shoots of *Inula viscosa* or *Inula graveolens* into an organic solvent or shaking the freshly cut or dried and ground leaves and stems of the shoots in an organic solvent for thirty minutes, and then evaporating the solvent to form a paste. The yield obtained by this method can be as much as 30%, in contrast to the low yields known in the literature and described above.

The medicinal properties of Inula extracts in humans are well known. For example, Debat disclosed the anti-microbial activity of extracts of Inula for use in human beings. However, the fungicidal effects of Inula extracts have only been demonstrated on fungi growing in Petri dishes or on post-harvest of fruits. For example, Qasem et al. (*Phytopathologia Mediterana,* 34:7–14, 1995) demonstrated that the growth of certain fungi in Petri dishes was inhibited by aqueous extracts of *Inula viscosa* as well as by dried plant material added directly to the fungal growth media. By contrast, the method of the present invention uses Inula extracts prepared with alkaline aqueous solvents used against fungal infections of crop plants themselves.

Clearly, although Inula extracts have been shown to have fungicidal activity in the Petri dish (in vitro) and on plant (in vivo), the methods of preparation for these extracts have not been sufficient for large scale use directly on crop plants and have had other serious disadvantages. The true effectiveness of these extracts against fungal infections of plants is, therefore, unknown. Furthermore, there is a clear need for better methods to prepare Inula extracts. Qasem et al. (Ibid, page 13, 1995) concluded: "The diversity and the methodology of extraction and the differences in the results obtained . . . increased the need for developing more efficient, convenient, and cheaper methods of extraction to facilitate more extensive utilization of fungicidal extracts, especially if greater quantity of extracts must be prepared for large-scale production".

Thus, there is a widely recognized need for and would be highly advantageous to have a method or methods for preparing extracts and/or suspensions of plants of Inula species which would facilitate the large-scale use of these extracts and suspensions which would simplify their preparation and use, be highly effective in controlling fungal infection in plants, as well as controlling fungal infections in crop plants.

SUMMARY OF THE INVENTION

According to the present invention, there is provided a method for preparing an aqueous extract from Inula species which comprises contacting shoots and/or portions thereof with an alkaline aqueous solvent to form a solution and debris, and removing the debris from the solution.

There is also provided a method for protecting plants against fungal infection comprising preparing a fungicidal extract of Inula species by contacting shoots and/or portions thereof with an alkaline aqueous solvent to form an extract solution and debris, and applying a fungicidally effective amount of the fungicidal extract to a plant for protecting the plant against fungal infection.

There is also provided in accordance with the present invention, a method for preparing a fungicide derived from Inula species which comprises combining a substantially powdered form of Inula shoots and/or portions thereof with a solid chemical to form a mixture which upon dissolution of the mixture in an aqueous solvent, forms an alkaline aqueous solution which can be directly applied to plants to prevent fungal infection.

Additionally, also in accordance with the present invention, there is provided an alkaline anti-fungal composition which comprises Inula shoots and/or portions thereof and a compound which when mixed with an aqueous solvent forms an alkaline solution, whereby the composition can be directly applied to plants to prevent fungal infection.

Accordingly, the subject invention provides a method for unexpectedly producing an anti-microbial extract from Inula plants which is not only active in vitro against fungi but also is active against diseases caused by fungi in crop plants while being safe to apply to the crop itself.

DETAILED DESCRIPTION OF THE INVENTION

The present invention provides a method for preparing an extract from Inula species including the steps of contacting shoots and/or portions thereof with an alkaline aqueous solvent to form a solution and debris and then removing the debris from the solution.

Preferably, the portion and/or portions of the Inula plant which are utilized in the present invention are the leaves and stem of the upper, younger parts of the shoots, and the upper part of the shoot extending from about 20–40 centimeters from the tip of the shoot. The flowers themselves are not used. As used herein, the term "shoot" is used to define the leaves and stem of the shoot of the Inula plant. In the methods of the present invention, the shoots or portions thereof can be either freshly cut or may be dried prior to the addition of the alkaline aqueous solvent.

The alkaline aqueous solvent can include any compound or compounds which alone or in solution have a pH which is greater than about seven such as an inorganic base or salt thereof.

Preferably, the alkaline aqueous solvent includes at least one of amino compound. The amino compound can include an ammonium compound, organic amines and/or heterocyclic amines. The organic amines can include compounds such as ethylamine, ethylenediamine, diaminopropane, diethanolamine, triethanolamine, and butylamnine. Heterocyclic compounds can include compounds such as piperazine and piperidine.

The removal of the debris from the solution can be accomplished by filtering the debris from the solution utilizing a screen such as a 100 micron μm (micron) sieve or other suitable filtering devices known to those skilled in the art.

If dried shoots and/or portions thereof are utilized in the method of the present invention, the dried shoots and/or portions thereof can be ground, by various means known to those skilled in the art, to form a powder.

In an embodiment of the invention, fresh Inula shoots are dipped in the alkaline solution for an appropriate period of time, typically for approximately 0.2–5 minutes. The plant material is then discarded and the solution, which may be colored, obtained therefrom is screened through a filter such as a 100 micron sieve and can be applied, as is, for spraying crop plants.

In another embodiment, fresh shoots are first air dried at 30–40° C. for period of time sufficient to dry the shoots, typically approximately 1–2 days and the dried shoots then dipped in the alkaline solution for a period of time which can be approximately 1–10 minutes. The plant material is discarded and the solution (colored) obtained can be filtered through a filter or sieve and then utilized, as is, for spraying crop plants.

In another embodiment, dried shoots obtained by air drying as described immediately above can be ground and then passed through a metal sieve (i.e., 2 mm). The ground plant material can then be shaken in an alkaline solution for 1–10 minutes, screened through a filtering device such as a 100 micron sieve, and the colored liquid obtained therefrom can be utilized for spraying crop plants.

In yet another embodiment, dried and ground plant material as immediately described above, can be placed in a mortar and is milled to less than 100 micron-sized particles to obtain a fine powder. The powder is then mixed with an alkaline solution and can be sprayed, as such, onto the crop plants.

In another embodiment, dried powder which is ground to less than 100 micron-sized particles is milled with crystallized cellulose (Avicel PH-101, Fluka) and is then mixed with the alkaline solution and sprayed directly onto crop plants.

In another embodiment, a dried powder which has been milled to less than 100 micron-sized particles is milled with a surfactant such as Vercoryl-S, diatomaceous earth, or sodium dodecyl sulfate and is then mixed with the alkaline solution and is sprayed directly onto the crop plants.

In another embodiment, dried Inula shoots ground to less then 100 micron-sized particles are mixed with a solid chemical, which upon dissolution in water, produces an alkaline solution. The solid chemical can be any of the compounds described above for the alkaline solution including an imidazole, dibasic ammonium phosphate, Trizmabase (Sigma) either with or without the addition of an inert surfactant formulation. The powder mixture is then mixed with water to form an anti-fungal agent and is sprayed directly onto crop plants. In this form, the anti-fungal agent can be prepared and/or sold as a dry mix which, when hydrated, forms an anti-fungal composition which can be easily applied to plants. In this form, the costs of shipping and/or transporting the anti-fungal material can be reduced since the water would only be added just prior to use/application to plants.

In another embodiment, the dried and ground Inula of particle size less than 100 microns can be mixed with $(NH_4)_2HPO_4$ (dibasic ammonium phosphate) and be suspended in water to which $NH_4OH$ is added. This solution can then be sprayed directly onto crop plants.

According to the present invention, there is also provided a method for protecting plants against fungal infections by the steps of (a) preparing a fungicidal extract of Inula species by contacting shoots and/or portions thereof with an alkaline aqueous solvent to form an extract solution and debris and (b) applying a fungicidally effective amount of the fungicidal extract to a plant for protecting a plant against fungal infection. As defined herein, a fungicidally effective amount includes such an amount that is capable of preventing, inhibiting, and/or killing fungus in or on a plant.

Solutions or emulsions containing the Inula extract, or the Inula suspension, are sprayed onto the upper leaf surfaces of various crop plants by well known techniques for the control of fungal plant infections. The Inula extracts of the present invention can be used to control fungal plant infections caused by fungi including, but not limited to, Oomycetes, Ascomycetes, Basidiomycetes, and *Fungi imperfecti* classes.

The method and fungicidal extracts of the present invention are particularly suitable for use against fungi of the Oomycetes, Ascomycetes, Basidiomycetes and *Fungi imperfecti* classes including but not limited to *Phytophthora infestans, Pseudoperonospora cubensis, Plasmopara viticola, Sphaerotheca fuliginea, Cladosporium*

*cucumerinum, Erysiphe graminis, Uromyces appendiculatus*, and *Botrytis cinera* and in crops including, but not limited to, grapevines, tomato, wheat, barley, tobacco, potatoes, onions, cucurbits, beans and crucifers.

Also according to the present invention, there is provided a method for preparing a fungicide derived from Inula species which includes combining a substantially powdered form of Inula shoots and/or portions thereof with a solid chemical to form a mixture which upon dissolution of the mixture and an aqueous solution, forms an alkaline aqueous solution which can be directly applied to plants to prevent fungal infection. Fungicides prepared by this method are described above and in the Example section below.

Also in accordance with the present invention, an alkaline anti-fungal composition of Inula shoots and/or portions thereof and a compound which when mixed with an aqueous solvent forms an alkaline solution which can be directly applied to plants to prevent fungal infection is disclosed. The compounds which can be mixed with an aqueous solution to form an alkaline solution are described above and in the Examples section below.

The invention of the present invention is illustrated below in the following Examples which describe the preparation and use of Inula extracts and suspensions against fungal infections in plants.

To test the efficacy of these extracts and suspensions, experiments were performed in which plants were sprayed using a fine glass atomizer with either Inula extract or with pure solvent as a control for the Inula extracts, with either Inula extract and emulsifier or with an emulsifier solution as a control for the emulsified Inula extracts, and with either Inula suspension or with water or emulsifier solution as a control for the Inula suspensions. Treated and control plants were then inoculated with a crop-respective fungal pathogen. After an incubation period, the extent of the infection was measured. Unless otherwise stated, percentage protection from the disease due to the treatment with the Inula extract or suspension was calculated as:

% control of the disease=[1−(% infection and treated plants/% infection in control plants)]×100.

The following experimental data illustrate the utility of the fungicidal compositions of the present invention.

EXAMPLES

Methods:

The crop plants and pathogens used for inoculation are described in the following list.

| crop plant | pathogen | disease |
|---|---|---|
| Tomato | *Phytophthora infestans* | late blight |
| Potato | " | " |
| Cucumber | *Pseudoperonospora cubensis* | downy mildew |
| Melon | " | " |
| Wheat | *Erysiphe graminis tritici* | powdery mildew |
| Cucumber | *Sphaerotheca fuliginea* | " |
| Melon | " | " |
| Tobacco | *Perenospora tabacina* | downy mildew |
| Grapes | *Plasmpara viticola* | " |
| Tomato | *Botrytis cinerea* | gray mold |
| Cucumber | " | " |
| Tomato | *Cladosporium fulvum* | leaf mold |

Inoculation with *P. infestants, P. cubensis, P. tabacina, P. viticola, B. cinera* and *C. fulvum* was done by spraying a spore suspension in distilled water onto the upper leaf surfaces of the treated (and the control) plants. Inoculated plants were kept in a dew chamber at 18–20° C. in the dark for 16–20 hours and then in a growth chamber at 20° C. with 12 hours photoperiod. Inoculation with *E. graminis* and *S. fuliginea* was done by blowing spores over the treated (and control) plants. Inoculated plants were then kept in a growth chamber as above.

Disease records were visually estimated in the inoculated plants at 3–13 days after inoculation, depending on the crop and disease. Percentage leaf area occupied with disease symptoms or fungal colonies was recorded and given in the results section.

Example 1

Activity of dipping extract of fresh Inula shoots in 0.1 N NaOH for ten minutes on disease development in crop plants.

| | % Diseased leaf area | |
|---|---|---|
| Extract | late blight in potato | powdery mildew in wheat |
| control untreated | 94 | 63 |
| original (pH 12.7) | 15 | 24 |
| diluted: 2 | 9 | 25 |
| diluted: 4 | 10 | 30 |
| diluted: 8 | 8 | 50 |
| original (neutralized to pH 7.2) | 5 | 12 |
| diluted: 2 | 94 | 18 |
| diluted: 4 | 95 | 25 |
| diluted: 8 | 95 | 30 |

50 g fresh weight shoots were dipped in 250 ml of 0.1 N NaOH for ten minutes. Half of the extract was sprayed (pH 12.7) after various dilutions and the other half was neutralized with HCl to pH 7.2 and then sprayed after various dilutions. Late blight and powdery mildew were inoculated one day after spray and disease records taken after four and eight days, respectively.

Example 2

Activity of dipping extracts of fresh Inula shoots in ammonium hydroxide (containing 25% $NH_3$ by weight) for ten minutes on late blight development in potato.

| Treatment | Diseased leaf area | % Protection |
|---|---|---|
| untreated control | 98 | — |
| $NH_4OH$ | | |
| 8% | 100 | 0 |
| (= 2% aqueous $NH_3$) | | |
| 4% | 100 | 0 |
| 2% | 100 | 0 |
| 1% | 100 | 0 |
| Inula in $NH_4OH$ | | |
| 8% | 10 | 90 |
| 4% | 20 | 80 |
| 2% | 50 | 50 |
| 1% | 88 | 12 |

60 g fresh weight shoot were dipped in 250 ml $NH_4OH$ solution for ten minutes. Extracts were sprayed after various dilutions onto potato plants and inoculated with *Phytophtera infestants* two days later. Disease was recorded four days post inoculation. $NH_4OH$ solutions of corresponding concentration were also sprayed for comparison. The % $NH_4OH$ throughout the Examples, where appropriate, refers to % from a liquid containing 250 g $NH_3$ per liter. For example, 8% $NH_4OH$ means 8 ml of a solution (containing 25% $NH_3$) per 100 ml water. To express % $NH_4OH$ as % $NH_3$, should divide by 4. Note: $NH_4OH$ was not phytotoxic.

Example 3
Efficacy of Inula extracts, made by dipping fresh shoots in $NH_4OH$ for ten minutes, in the control of late blight in potato (a) and powdery mildew in wheat (b).

| | | % blighted leaf area | | |
|---|---|---|---|---|
| | | | 3 d - old extract | |
| $NH_4OH$ conc., % | fresh extract | 1 d - old extract | a | b |
| untreated control | 100 | 100 | 100 | 75 |
| 1 | 23 | 63 | 25 | 23 |
| 2 | 5 | 13 | 23 | 1 |
| 4 | 8 | 18 | 8 | 11 |
| 8 | 8 | 10 | 25 | 24 |
| 16 | 3 | 10 | 5 | 6 |

One Inula shoot (10 g fresh weight) was dipped in 50 ml of $NH_4OH$ of various concentrations for ten minutes and the extract sprayed onto potato plants one or three days later. Plants were inoculated with *P. infestants* or *E. graminis* one day later and disease records taken seven days post inoculation.

Example 4
Activity, after storage, of fresh shoot Inula extract made with ammonium hydroxide against fungal diseases of crop plants.

| | | % diseased leaf area | | | |
|---|---|---|---|---|---|
| $NH_4OH$ conc., % | storage period, days | late blight in potato, 5 d | downy mildew in melon 6 d | powdery mildew in wheat 7 d | downy mildew in grapes 10 d |
| control untreated | 1 | 98 | 81 | 100 | 50 |
| 0.25 | | 38 | 15 | 50 | 20 |
| 0.5 | | 15 | 4 | 13 | 15 |
| 1.0 | | 8 | 1 | 1 | 5 |
| control untreated | 9 | 98 | 50 | | |
| 0.25 | | 69 | 38 | | |
| 0.5 | | 13 | 13 | | |
| 1.0 | | 13 | nd | | |
| control untreated | 18 | | | 75 | |
| 0.25 | | | | nd | |
| 0.5 | | | | 0 | |
| 1.0 | | | | 0 | |
| control untreated | 60 | | 95 | | |
| 0.25 | | | 38 | | |
| 0.5 | | | 21 | | |
| 1 | | | 18 | | |

100 g fr. w. shoot were shaken for 10 minutes in 1 L of $NH_4OH$. Plant material discarded and the extract was sprayed onto the crop plants.
nd = not done.

Example 5
Activity of aqueous or acetone extracts made from dry crushed shoots of Inula against fungal diseases of crop plants.

| | % Diseased leaf area | | | |
|---|---|---|---|---|
| solvent | late blight in potato 4 d | downy mildew in cucumber 6 d | powdery mildew in cucumber 6 d | powdery mildew in wheat, 8 d |
| untreated control | 83 | 88 | 88 | 88 |
| water | 18 | 5 | 75 | 63 |
| KOH 0.1N | 88 | 4 | 75 | 63 |
| NaOH 0.1N | 63 | 28 | 50 | 25 |
| $NH_4OH$ 1.4% | 1 | 8 | 50 | 13 |
| $NH_4OH$ 7% | 3 | 4 | 25 | 15 |
| $(NH_4)_2HPO_4$ 0.1M (1.3%) | 0.3 | 0 | 50 | 3 |
| $K_2HPO_4$ 0.1M | 23* | 3 | 88 | 20 |
| Acetone | 8 | 3 | 25 | 5 |

1 g dry crushed shoots were shaken for thirty minutes in 50 ml of the solvent, screened (100μ) and sprayed onto the crop plants. Plants were inoculated one day after spray,
*phytotoxic Example 6
Activity of dry crushed Inula shoots extracted with ammonium hydroxide and ammonium phosphate (dibasic) against fungal disease in crop plants.

| | | % diseased leaf area | | | | |
|---|---|---|---|---|---|---|
| solvent, conc. | pH | late blight in tomato 4 d | late blight in potato 6 d | downy mildew in cucumber 8 d | powdery mildew in wheat 11 d | powdery mildew in melon* 14 d |
| None | — | 88 | 100 | 100 | 100 | 180 |
| $(NH_4)_2HPO_4$ 1.32% (0.1M) | 7.9 | 25 | 14 | 16 | 18 | 150 |
| $NH_4OH$ 0.7% (0.1M) | 10.97 | 25 | 22 | 28 | 15 | 55 |
| $(NH_4)_2HPO_2$ + $NH_4OH$, mixed, 0.1M | | | | | | |
| 9 + 1 | 8.25 | 29 | 5 | 27 | 15 | 80 |
| 7.5 + 2.5 | 8.6 | 31 | 13 | 16 | 3 | 100 |
| 5 + 5 | 9.0 | 11 | 6 | 6 | 0 | 40 |
| 2.5 + 7.5 | 9.4 | 20 | 0 | 11 | 1 | 25 |
| 1 + 9 | 9.8 | 16 | 2 | 16 | 8 | 20 |
| water | 6.2 | 75 | 80 | 58 | 75 | 180 |
| acetone | — | 0 | 16 | 11 | 8 | 130 |

1 g crushed dry shoots were shaken for five minutes in 50 ml of solvent, screened and sprayed. Innoculation took place three hours after spray,
*Number of fungal colonies per plant. Extracts were used six days after preparation.
The molarity of $NH_4OH$ is based on molecular weight of 35.

Example 7
Activity of crushed dry Inula shoots extracts made with aqueous solutions of ethylamine and ethylenediamine against fungal diseases of crop plants.

| solvent, conc. and pH | Potato late blight 4 d % blighted leaf area | cucumber downy mildew 6 d lesions/plant |
|---|---|---|
| control untreated | 94 | 125 |
| ethylamine 0.7% (pH 12.3) | 15 | 5 |

| solvent, conc. and pH | Potato late blight 4 d % blighted leaf area | cucumber downy mildew 6 d lesions/plant |
|---|---|---|
| ethylenediamine 0.6% (pH 11.95) | 50 | 4 |

1 g dry crushed shoots of Inula were shaken for five minutes in 50 ml of the aqueous solvent, screened and sprayed onto the plants. Plants were inoculated one day after spray.

Example 8

Activity of alkaline extracts or acetone of fresh Inula shoots against disease development in crop plants.

| | % infected leaf area | |
|---|---|---|
| solvent and conc. | late blight in tomato 6 d | powdery mildews in wheat 11 d |
| untreated control | 88 | 75 |
| ethylamine, 1% | 0 | 38 |
| ethylenediamine, 0.9% | 0 | 38 |
| ammonium hydroxide, 1% (0.25% $NH_3$ in water) | 1 | 20 |
| 2-amino-2-methylpropanole (AMP) 0.9% | 25 | nt |
| acetone | 0 | 23 |

25 g fresh shoots of Inula were dipped for ten minutes in 250 ml of the solvent, and the extracts sprayed onto crop plants. Inoculation took place three hours after spray.

Example 9

Sequential extraction of fresh Inula shoots with acetone and ammonium hydroxide and the activity of the extract against plant disease.

| | | % infected leaf area | |
|---|---|---|---|
| First solvent | Second solvent | late blight in tomato, 6 d | powdery mildews in wheat, 11 d |
| untreated | control | 88 | 75 |
| $NH_4OH$, 1% | — | 1 | 20 |
| acetone | — | 0 | 23 |
| $NH_4OH$, 1% | acetone | 1 | 25 |
| acetone | $NH_4OH$, 1% | 38 | 75 |

25 g fresh Inula shoots were dipped for ten minutes in the first solvent. Then washed with water, blotted dry and dipped for ten minutes in the second solvent. Extracts were sprayed onto the crop plants before inoculation.

Example 10

Antimicrobial activity, in vitro, of alkaline extracts of fresh Inula shoots.

| extraction made with | fungal colonies per dish | bacterial colonies per dish |
|---|---|---|
| no extract, control | 75 | 30 |
| ethylamine, 1% | 7 | 30 |
| ethylene diamine, 0.9% | 10 | 40 |
| ammonium hydroxide, 1% | 12 | 15 |
| acetone (positive control) | 4 | 0 |

0.5 ml extract (see Example 8) was pipetted onto a 9 cm diam petri dish containing 10 ml Potato Dextrose Agar. Dishes were exposed to aerial contamination for ten minutes. Dishes incubated at 25° C. for four days until data were collected.

Example 11

Dose-dependent activity of alkaline extracts made from dry crushed Inula shoots with 1:1 mixture (pH 9.0) of 0.1M (1.32%) $(NH_4)_2HPO_4$ and 0.1M (0.7%) $NH_4OH$, against late blight in tomato.

| g dry shoots per 50 ml solvent | blighted leaf area %, 4 days |
|---|---|
| untreated control | 88 |
| solvent control | 88 |
| 0.1 | 75 |
| 0.2 | 63 |
| 0.4 | 25 |
| 0.6 | 25 |
| 0.8 | 18 |
| 1 | 14 |
| 2 | 3 |

0.1–2 g dry crushed shoots were shaken for five minutes in 50 ml of the solvent mixture, screened and sprayed. Inoculation took place three hours later.

Example 12

Activity of aqueous alkaline extracts made from dry crushed Inula shoots against late blight in tomato.

| | % diseased leaf area | |
|---|---|---|
| solvent | Inula extract | solvent control |
| untreated control | 81 | — |
| piperazine hydrate 0.05M (1%) pH 11.3 | 3 | 81 |
| piperazine hydrate 0.1M (2%) pH 11.3 | 3 | 81 |
| triethanolamine 0.1M (1.59%) pH 10.3 | 23 | 81 |

1 g dry crushed shoots was shaken in 50 ml of the solvent for one hour, screened and sprayed. Plants were inoculated three hours after spray and disease was recorded four days later.

Example 13

The effect of concentration of piperazine hydrate on the activity of Inula extracts against late blight in tomato and potato.

| piperazine hydrate | % diseased leaf area | |
|---|---|---|
| conc., % | tomato | potato |
| 0 | 91 | 95 |
| 0.06 | 18 | 25 |
| 0.12 | 11 | 25 |
| 0.25 | 4 | 25 |
| 0.50 | 18 | 44 |
| 1.00 | 0 | 75 |
| 2.00 (= 0.1M) | 8 | 75 |

1 g dry crushed Inula shoots was shaken for one hour in 50 ml of piperazine solutions, screened and sprayed. Inoculation was done three hours after spray and disease recorded five days after inoculation.

Example 14
Efficacy of tetraethylene or piperidine aqueous solutions on extraction of antifungal components from dry shoots of Inula.

| | % diseased leaf area | | |
|---|---|---|---|
| Treatment | Tomato late blight, 4 d | cucumber downy mildew, 6 d | wheat powdery mildew, 10 d |
| none (control) | 88 | 88 | 50 |
| tetraethylene 1% (pH 11.2) | 63 | 31 | 50 |
| piperidine 1% (pH 12.0) | 88 | 94 | 25 |
| Inula in tetraethylene 1% | 25 | 47 | 50 |
| Inula in piperidine 1% | 25 | 1 | 13 |

1 g dry crushed Inula shoots was shaken for ten minutes in 50 ml of the solvent, screened and sprayed. Inoculation was done three hours after spray.

Example 15
Activity of aqueous alkaline or acetone extracts made from Inula shoots against mildews in cucumber and wheat.

| | % diseased leaf area | | |
|---|---|---|---|
| solvent | downy mildew in cucumber 6 d | powdery mildew in cucumber 11 d | powdery mildew in wheat 8 d |
| untreated control | 75 | 100 | 100 |
| Trizma-base ® (Sigma) 1% | 20 | 13 | 3 |
| piperazine hydrate 1% | 18 | 38 | 38 |
| piperadine 1% | 5 | 25 | 18 |
| imidazole 1% | 0 | 0 | 0 |
| acetone (positive control) | 2 | 25 | 25 |

1 g dry crushed leaves of Inula was shaken for ten minutes in 50 ml of the solvent, screened and sprayed. Inoculation was done three hours after spray.

Example 16
Efficacy of sec-butylamine in extracting antifungal components from dry Inula shoots.

| sec-butyl-amine conc., % | lesions per plant late blight in potato 3 d | % diseased leaf area | | |
|---|---|---|---|---|
| | | late blight tomato 4 d | powdery mildew cucumber 13 d | wheat 7 d |
| 0 | 130 | 88 | 88 | 100 |
| 0.06 | 60 | 63 | 14 | 23 |
| 0.12 | 0 | 25 | 14 | 0 |
| 0.25 | 5 | 8 | 9 | 15 |
| 0.5 | 0 | 15 | 15 | 3 |
| 1.0 (pH 11.5) | 2 | 3 | 9 | 5 |

1 g dry crushed Inula shoots was shaken for ten minutes in 50 ml of sec-butylamine, screened and sprayed. Inoculation was done three hours after spray.

Example 17
Efficacy of imidazole in extracting antifungal component from dry Inula shoots.

| | % diseased leaf area | | |
|---|---|---|---|
| Treatment | late blight tomato, 5 d | late blight potato, 5 d | powdery mildew wheat, 8 d |
| none | 81 | 100 | 69 |
| Imidazole only | | | |
| 0.12% pH 9.55 | 95 | 50 | 63 |
| 0.25% pH 9.70 | 88 | 50 | 50 |
| 0.5% pH 9.86 | 69 | 25 | 23 |
| 1% pH 9.95 | 50 | 18 | 25 |
| Inula extract in imidazole | | | |
| 0.12% | 30 | 5 | 0 |
| 0.25% | 20 | 18 | 18 |
| 0.5% | 30 | 30 | 0 |
| 1.0% | 30 | 15 | 0 |
| Inula in acetone | 5 | 0 | 3 |

1 g of dry crushed Inula shoots was shaken in 50 ml of imidazole for ten minutes, screened and sprayed. Inoculation was done three hours after spray.

Example 18
Composition of a 50 WP formulation of Inula shoots and its activity against fungal plant diseases.

Composition:
5 g dry Inula shoot powder
2.5 g imidazole
2.5 g inert carriers and surfactants (Sandoz)

| Activity | | % diseased leaf area | | |
|---|---|---|---|---|
| g product per 50 ml water | pH | late blight tomato 5 d | late blight potato 5 d | powdery mildew wheat 13 d |
| 0 | — | 98 | 100 | 38 |
| 0.25 | 8.20 | 75 | 75 | 25 |
| 0.5 | 8.21 | 38 | 63 | 13 |
| 0.75 | 8.22 | 31 | 25 | 0 |
| 1 | 8.23 | 23 | 18 | 0 |
| 1.25 | 8.24 | 20 | 20 | 0 |

-continued

| Activity | | % diseased leaf area | | |
|---|---|---|---|---|
| g product per 50 ml water | pH | late blight tomato 5 d | late blight potato 5 d | powdery mildew wheat 13 d |
| 1.5 | 8.25 | 15 | 13 | 0 |
| 2 | 8.25 | 1 | 10 | 0 |

Example 19
Composition of a 50 WP formulation of Inula shoots and its activity against fungal plant diseases.
Composition:
5 g dry Inula shoot powder
3.75 g imidazole
1.25 g inert carriers and surfactants (Sandoz)

| Activity | | % diseased leaf area | | |
|---|---|---|---|---|
| g product per 50 ml water | pH | late blight tomato 4 d | late blight potato 5 d | powdery mildew wheat 9 d |
| 0 | — | 95 | 81 | 38 |
| 0.25 | 8.28 | 75 | 69 | 25 |
| 0.5 | 8.29 | 63 | 25 | 0 |
| 0.75 | 8.32 | 38 | 15 | 0 |
| 1 | 8.33 | 25 | 13 | 0 |
| 1.25 | 8.35 | 21 | 13 | 0 |
| 1.5 | 8.36 | 13 | 18 | 0 |
| 2 | 8.37 | 6 | 8 | 0 |

Example 20
Composition of 45 WP formulation of Inula shoots and its activity against fungal plant diseases.
Composition:
5 g dry Inula shoot powder
5 g imidazole
1 g inert carriers and surfactants (Sandoz)

| Activity g product per 50 ml water | pH | % diseased leaf area late blight in tomatoes 4 d |
|---|---|---|
| 0 | — | 75 |
| 0.25 | 8.18 | 75 |
| 0.5 | 8.23 | 50 |
| 0.75 | 8.28 | 50 |
| 1 | 8.29 | 38 |
| 1.5 | 8.30 | 25 |
| 2 | 8.38 | 3 |

Example 21
Composition of 50 WP formulation of Inula shoots and its activity against fungal plant diseases.
Composition:
5 g dry Inula shoot powder
2.5 g dibasic ammonium phosphate
2.5 g Avicel P-101® (Fluka)=crystalline cellulose

| Activity g product per 50 ml water | pH | % diseased leaf area | | | |
|---|---|---|---|---|---|
| | | late blight in tomato, 4d | late blight in potato, 6 d | downy mildew in cucumber, 6 d | powdery mildew in wheat, 9 d |
| 0 | — | 98 | 98 | 50 | 75 |
| 0.1 | 7.33 | 75 | 93 | 13 | 75 |
| 0.2 | 7.44 | 75 | 93 | 8 | 50 |
| 0.4 | 7.46 | 63 | 38 | 3 | 50 |
| 0.6 | 7.46 | 63 | 30 | 1 | 25 |
| 0.8 | 7.46 | 18 | 23 | 3 | 23 |
| 1 | 7.46 | 23 | 20 | 0 | 20 |
| 1.5 | 7.46 | 23 | 18 | 0 | 18 |

Example 22
Composition of 50 WP formulation of Inula shoots and its activity against fungal plant diseases.
Composition:
5 g dry Inula shoot powder
2.5 g Trizma-Base® (Sigma)
2.5 g Avicel PH-101® (Fluka)

| Activity | | % diseased leaf area | | |
|---|---|---|---|---|
| g product per 50 ml water | pH | late blight tomato, 3d | late blight in potato, 5 d | powdery mildew in wheat, 8 d |
| 0 | — | 95 | 95 | 75 |
| 0.2 | 8.55 | 88 | 95 | 50 |
| 0.4 | 8.62 | 88 | 93 | 50 |
| 0.6 | 8.67 | 38 | 69 | 25 |
| 0.8 | 8.68 | 23 | 38 | 25 |
| 1 | 8.70 | 30 | 25 | 25 |
| 1.5 | 8.72 | 23 | 25 | 25 |
| 2 | 8.74 | 25 | 25 | 25 |

Example 23
Composition of 50 WP formulation of Inula shoots and its activity against fungal plant diseases.
Composition:
5 g dry Inula shoot powder
5 g dibasic ammonium phosphate

| Activity g product per 50 ml water | pH | % diseased leaf area | | | |
|---|---|---|---|---|---|
| | | late blight in tomato, 4 d | late blight in potato lesions/plant 3 d | late blight in potato lesions/plant 4 d | powdery mildew in wheat, 7 d |
| 0 | — | 95 | >500 | 88 | 88 |
| 0.2 | 7.42 | 38 | 200 | 69 | 38 |

-continued

| Activity g product per 50 ml water | pH | late blight in tomato, 4 d | late blight in potato lesions/plant 3 d | 4 d | powdery mildew in wheat, 7 d |
|---|---|---|---|---|---|
| 0.4 | 7.45 | 25 | 180 | 69 | 38 |
| 0.6 | 7.45 | 23 | 50 | 25 | 23 |
| 0.8 | 7.45 | 20 | 40 | 25 | 13 |
| 1 | 7.46 | 3 | 20 | 20 | 13 |
| 2 | 7.47 | 1 | 5 | 8 | 3 |

Example 24

Composition of alkaline wettable powder formulations of Inula used to control plant diseases.

| Formula | Percent a-i | Alkaline agent | pH | Other component |
|---|---|---|---|---|
| Inula leaves (27%) Zeofree 80 (60%) Polyfon F (3%) Synfactant (10%) | 25 | none | 6.8 | |
| Inula leaves (25%) Zeofree 80 (62%) Polyfon F (3%) Monoamine 779 (10%) | 25 | amines (10%) | 7.9 | |
| Inula leaves (25%) Zeofree 80 (95%) Stepsperse DF500 (10%) Monoamine 779 (20%) Triethanolamine (50%) | 12.5 | triethanolamines | 8.5 | |
| Inula leaves (25%) Zeofree 80 (25%) diammonium phosphate (25%) Reax M100 (5%) Kaolin (20%) | 25 | $(NH_4)_2HPO_4$ (25%) | 7.5 | |
| Inula leaves (25%) Hubersorb 600 (25%) diammonium phosphate (25%) Reax M100 (5%) Kaolin (20%) | 25 | $(NH_4)_2HPO_4$ (25%) | 8 | |
| Inula leaves (25%) Hubersorb 600 (40%) diammonium phosphate (25%) Stepan DF 500 (10%) | 25 | $(NH_4)_2HPO_4$ (25%) | 8 | |
| Inula leaves (25%) Hubersorb 600 (24%) diammonium phosphate (25%) Stepan DF 500 (5%) 40% Tdet 09 on Zeolex 7A (5%) | 25 | $(NH_4)_2HPO_4$ (25%) | 8 | |

Example 25

Late blight in potato.

| Formulation | % infected leaf area 6 days Conc. % a-i | | | |
|---|---|---|---|---|
| | 0 | 0.25 | 0.5 | 1.0 |
| Inula leaves (27%) Zeofree 80 (60%) Polyfon F (3%) Synfactant (10%) | 100 | 100 | 100 | 100 |
| Inula leaves (25%) Zeofree 80 (62%) Polyfon F (3%) Monoamine 779 (10%) | | 50 | 25 | 38 |
| Inula leaves (25%) Zeofree 80 (95%) Stepsperse DF500 (10%) Monoamine 779 (20%) Triethanolamine (50%) | 25 | 25 | 25 | 18 |
| Inula leaves (25%) Zeofree 80 (25%) diammonium phosphate (25%) Reax M100 (5%) Kaolin (20%) | | 100 | 69 | 50 |

-continued

| Formulation | % infected leaf area 6 days Conc. % a-i | | | |
|---|---|---|---|---|
| | 0 | 0.25 | 0.5 | 1.0 |
| Inula leaves (25%) Hubersorb 600 (25%) diammonium phosphate (25%) Reax M100 (5%) Kaolin (20%) | | 100 | 50 | 20 |
| Inula leaves (25%) Hubersorb 600 (40%) diammonium phosphate (25%) Stepan DF 500 (10%) | | 50 | 20 | 0 |
| Inula leaves (25%) Hubersorb 600 (24%) diammonium phosphate (25%) Stepan DF 500 (5%) 40% Tdet 09 on Zeolex 7A (5%) | | 100 | 88 | 25 |

Example 26

Late blight in tomato. Suspensions were used ~100 hours after preparation.

| Formulation | % infected leaf area 4 days Conc. % a-i | | | |
|---|---|---|---|---|
| | 0 | 0.25 | 0.5 | 1.0 |
| Inula leaves (27%) Zeofree 80 (60%) Polyfon F (3%) Synfactant (10%) | 95 | 88 | 75 | 38 |
| Inula leaves (25%) Zeofree 80 (62%) Polyfon F (3%) Monoamine 779 (10%) | | 19 | 15 | 8 |
| Inula leaves (25%) Zeofree 80 (95%) Stepsperse DF500 (10%) Monoamine 779 (20%) Triethanolamine (50%) | | 18 | 1 | 0 |
| Inula leaves (25%) Zeofree 80 (25%) diammonium phosphate (25%) Reax M100 (5%) Kaolin (20%) | | 75 | 63 | 25 |
| Inula leaves (25%) Hubersorb 600 (25%) diammonium phosphate (25%) Reax M100 (5%) Kaolin (20%) | | 75 | 63 | 25 |
| Inula leaves (25%) Hubersorb 600 (40%) diammonium phosphate (25%) Stepan DF 500 (10%) | | 50 | 38 | 9 |
| Inula leaves (25%) Hubersorb 600 (24%) diammonium phosphate (25%) Stepan DF 500 (5%) 40% Tdet 09 on Zeolex 7A (5%) | | 75 | 38 | 19 |

Example 27

Downy mildew in cucumber.

| Formulation | % infected leaf area 6 days Conc. % a-i | | | |
|---|---|---|---|---|
| | 0 | 0.25 | 0.5 | 1.0 |
| Inula leaves (27%) Zeofree 80 (60%) Polyfon F (3%) Synfactant (10%) | 100 | 63 | 38 | 38 |
| Inula leaves (25%) Zeofree 80 (62%) Polyfon F (3%) Monoamine 779 (10%) | | 38 | 38 | 10 |
| Inula leaves (25%) Zeofree 80 (95%) Stepsperse DF500 (10%) Monoamine 779 (20%) Triethanolamine (50%) | | 20 | 20 | 13 |
| Inula leaves (25%) Zeofree 80 (25%) diammonium phosphate (25%) Reax M100 (5%) Kaolin (20%) | | 50 | 30 | 30 |
| Inula leaves (25%) Hubersorb 600 (25%) diammonium phosphate (25%) Reax M100 (5%) Kaolin (20%) | | 44 | 13 | 13 |
| Inula leaves (25%) Hubersorb 600 (40%) diammonium phosphate (25%) Stepan DF 500 (10%) | | 44 | 8 | 8 |
| Inula leaves (25%) Hubersorb 600 (24%) diammonium phosphate (25%) Stepan DF 500 (5%) 40% Tdet 09 on Zeolex 7A (5%) | | 75 | 63 | 44 |

Example 28

Downy mildew in grapes.

| Formulation | % sporulating leaf area 8 days Conc. % a-i | | | |
|---|---|---|---|---|
| | 0 | 0.25 | 0.5 | 1.0 |
| Inula leaves (27%) Zeofree 80 (60%) Polyfon F (3%) Synfactant (10%) | 97 | 60 | 5 | 0 |
| Inula leaves (25%) Zeofree 80 (62%) Polyfon F (3%) Monoamine 779 (10%) | | 25 | 25 | 20 |
| Inula leaves (25%) Zeofree 80 (95%) Stepsperse DF500 (10%) Monoamine 779 (20%) Triethanolamine (50%) | | 50 | 25 | 15 |
| Inula leaves (25%) Zeofree 80 (25%) diammonium phosphate (25%) Reax M100 (5%) Kaolin (20%) | | 70 | 15 | 0 |
| Inula leaves (25%) Hubersorb 600 (25%) diammonium phosphate (25%) Reax M100 (5%) Kaolin (20%) | | 60 | 20 | 20 |

-continued

| Formulation | % sporulating leaf area 8 days Conc. % a-i | | | |
|---|---|---|---|---|
| | 0 | 0.25 | 0.5 | 1.0 |
| Inula leaves (25%) Hubersorb 600 (40%) diammonium phosphate (25%) Stepan DF 500 (10%) | | 50 | 25 | 20 |
| Inula leaves (25%) Hubersorb 600 (24%) diammonium phosphate (25%) Stepan DF 500 (5%) 40% Tdet 09 on Zeolex 7A (5%) | | 80 | 80 | 50 |

Example 29
Powdery mildew in wheat.

| Formulation | % infected leaf area 8 days Conc. % a-i | | | |
|---|---|---|---|---|
| | 0 | 0.25 | 0.5 | 1.0 |
| Inula leaves (27%) Zeofree 80 (60%) Polyfon F (3%) Synfactant (10%) | 50 | 50 | 25 | 13 |
| Inula leaves (25%) Zeofree 80 (62%) Polyfon F (3%) Monoamine 779 (10%) | | 25 | 13 | 0 |
| Inula leaves (25%) Zeofree 80 (95%) Stepsperse DF500 (10%) Monoamine 779 (20%) Triethanolamme (50%) | | 25 | 13 | 0 |
| Inula leaves (25%) Zeofree 80 (25%) diammonium phosphate (25%) Reax M100 (5%) Kaolin (20%) | | 38 | 19 | 13 |
| Inula leaves (25%) Hubersorb 600 (25%) diammonium phosphate (25%) Reax M100 (5%) Kaolin (20%) | | 38 | 25 | 13 |
| Inula leaves (25%) Hubersorb 600 (40%) diammonium phosphate (25%) Stepan DF 500 (10%) | | 30 | 25 | 0 |
| Inula leaves (25%) Hubersorb 600 (24%) diammonium phosphate (25%) Stepan DF 500 (5%) 40% Tdet 09 on Zeolex 7A (5%) | | 25 | 25 | 5 |

In view of the teachings presented herein, other modifications and variations of the present inventions will be readily apparent to those of skill in the art. The foregoing discussion, and description are illustrative of some embodiments of the present invention, but are not meant to be limitations on the practice thereof. It is the following claims, including all equivalents, which define the scope of the invention.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, and specific compositions described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for preparing a fungicide derived from Inula species, the method comprising subjecting Inula shoot material to aqueous alkaline conditions to thereby form an alkaline aqueous extract, said alkaline aqueous extract having fungicidal activity.

2. A method according to claim 1, wherein the alkaline aqueous extract is generated by adding to an aqueous solution, a powdered form of said Inula shoot material and a solid chemical comprising at least one amino compound.

3. A method according to claim 2, wherein the amino compound comprises an ammonium compound.

4. A method according to claim 2, wherein the amino compound is selected from the group consisting of an organic amine and a heterocyclic amine.

5. A method according to claim 4, wherein the organic amine compound is selected from the group consisting of ethylamine, ethelenediamine, diaminopropane, diethanolamine, triethanolamine, and butylamine.

6. A method according to claim 4, wherein the heterocyclic amine is selected from the group consisting of piperazine and piperidine.

7. A method according to claim 2, wherein the solid chemical comprises at least one inorganic base or salts thereof.

8. A method according to claim 2, wherein the aqueous solution comprises an emulsifier.

9. A method according to claim 8, wherein the emulsifier comprises a surfactant.

10. A method according to claim 9, wherein the surfactant comprises sodium dodecyl sulfate.

11. A method according to claim 8, wherein the emulsifier comprises diatomaceous earth.

* * * * *